(12) United States Patent
Takenaka

(10) Patent No.: US 6,294,670 B1
(45) Date of Patent: Sep. 25, 2001

(54) PROBE FOR DETECTING A HIGHLY ORDERED STRUCTURAL SITE OF A SINGLE STRANDED NUCLEIC ACID OF A GENE, AND A METHOD AND A DEVICE FOR DETECTING THE SAME

(75) Inventor: Shigeori Takenaka, Koga (JP)

(73) Assignee: Kyushu University (JP)

( * ) Notice: Subject to any disclaimer, the term of this patent is extended or adjusted under 35 U.S.C. 154(b) by 0 days.

(21) Appl. No.: 09/313,992

(22) Filed: May 19, 1999

(30) Foreign Application Priority Data

Aug. 11, 1998 (JP) .................................................. 10-227019

(51) Int. Cl.$^7$ ....................................................... C07F 1/00
(52) U.S. Cl. ................................. 544/225; 544/224; 435/6
(58) Field of Search ................................. 544/225; 435/6

(56) References Cited

FOREIGN PATENT DOCUMENTS 9-288080    11/1997 (JP) .

OTHER PUBLICATIONS

Carey "Organic Chemistry: Second Edition" pp. 110–112, McGraw–Hill, New York 1992.*

Takenaka et al., "Enhanced electron transfer from glucose oxidase to a DNA–immobilized electrode aided by ferrocenyl naphthalene diimide, a threading intercalator" Chemistry Letters, pp. 989–990, 1998.*

Takenaka et al., "Electrochemically active threading intercaltor with high double stranded DNA selectivity" Chem. Commun., pp. 1111–1112, 1998.*

Okamura et al., "An amide–linked ferricene dimer, [(CH3CONHC5H4)Fe(C5H4CONHC5H4)Fe(C5H4CONHCH3]. Formation of inter–and intramolecular NH—O+ C hydrogen bonds." Inorganic Chemistry vol. 37, pp. 6731–6736, 1998.*

* cited by examiner

Primary Examiner—John S. Brusca
Assistant Examiner—Jeffrey S. Lundgren
(74) Attorney, Agent, or Firm—Burns, Doane, Swecker & Mathis, L.L.P.

(57) ABSTRACT

The invention provides a probe for detecting a highly ordered structural site of a nucleic acid of a gene by specifically binding with the structural site to generate an electrochemical response. The inventive probe comprises a cyclic ligand containing ferrocenyl group and a DNA threading intercalating moiety, such as 1, 4, 5, 8-tetrasubstituted naphthalene, 9, 10-disubstituted anthracene, and 1, 5-disubstituted anthraquinone. Current of the cyclic ligand is not observed due to interaction such as stacking or so called charge transfer between ferrocenyl group and the DNA threading intercalating moiety in conventional electrolyte. The binding of the ligand with a highly ordered structural site of a single stranded nucleic acid, where nucleic base inserts between the cavity of cyclic ligand, inhibits the intramolecular interaction of the ligand to convert the ligand into its electrically active form, and as a result, current is observed.

5 Claims, 2 Drawing Sheets

PROBE FOR DETECTING A HIGHLY ORDERED STRUCTURAL SITE OF A SINGLE STRANDED NUCLEIC ACID OF A GENE, AND A METHOD AND A DEVICE FOR DETECTING THE SAME

BACKGROUND OF THE INVENTION

1. Field of the Invention

The invention relates to a probe for detecting a highly ordered structural site of a single stranded nucleic acid of a gene, a method for detecting the same using the probe, and a device for detecting the same.

2. Related Arts

Sensors and sensing techniques have been utilized in every field of industries. In particular in biotechnology field, a high-sensitivity sensor system utilizing an enzyme reaction has been established. Recently, importance of gene sensing is increasing in applications such as gene therapy and gene diagnosis. Up to now, "DNA probe method" has been accepted as such gene sensing method.

A highly ordered structural site of a single stranded nucleic acid is a region located in a part of high-order structure of a DNA or RNA where the bases of the single stranded nucleic acids are not stacked, the region including a mismatch structure of an oncogenic DNA, a hairpin structure of a viral RNA and a bulge.

Such DNA probe method is mostly carried out by manual operations. Consequently, it has been demanded a gene sensor other than the DNA probe type sensor for detecting efficiently a specialized nucleic acid region of a gene. However, such sensor has not yet been reported or patented.

The object of the invention is to provide a detection probe for detecting a highly ordered structural site of a single stranded nucleic acid of a gene, and to provide a detection method and device using such probe.

The invention provides a probe for detecting a highly ordered structural site of a single stranded nucleic acid of a gene by specifically binding with the site to generate an electrochemical response, the probe comprising a cyclic ligand containing ferrocenyl group and a DNA threading intercalating moiety.

The DNA threading intercalating moiety is a moiety or residual group derived from a DNA threading intercalating compound. The DNA threading intercalating compound is a compound which can intercalate or slide between adjacent base pairs of a double stranded DNA with its two substituents projecting out of the major and minor groove simultaneously.

The invention also provides a method for detecting a highly ordered structural site of a single stranded nucleic acid of a gene, the method comprising:

contacting a gene to be detected with the above probe to generate an electrochemical response; and detecting the electrochemical response.

The inventors successfully developed a cyclic ligand, whose target is a highly ordered structural site of a single stranded nucleic acid of a gene, generating an electrochemical response only when such site is present in the gene. The probe may thereby provide a system for sensing a highly ordered structural site of a single stranded nucleic acid of a DNA or RNA with efficiency and high sensitivity. Moreover, in prior DNA probes, different DNA probes are required and provided responding to different target genes. On the contrary, the inventive detection probe may be applied to every gene having a highly ordered structural site of a single stranded nucleic acid.

The site of a gene is a part of a high-order structure in a DNA or RNA, including a mismatch structure frequently seen in an oncogenic DNA, an RNA hairpin structure of a virus, and a bulge structure. Such structural site comprises basically a single stranded structure, which usually coexists with a double stranded structure, causing some deformation in the structural site compared with a common single stranded nucleic acid structure. If the site structure is consecutive (such as in the case of a bulge or hairpin structure), it has a unique stacking structure entirely different from that of a common single stranded nucleic acid. For example, the onset of fragile X syndrome is deeply influenced by repeated hairpin structures. An HIV virus also preserves mismatch, hairpin and bulge structures present in its TAR-RNA and REE RNA, and such structures are indispensable for expressing the function of a HIV virus.

In the invention, ferrocene and naphthalene diimide (naphthalene bis(dicarboximide) or naphthalene-1,8; 4,5-diimide)) are condensed to obtain a cyclic ligand. Manufacturing example of the cyclic ligand is shown in FIG. 1. This representative cyclic ligand is named "cyclic naphthalene-diimideferrocene" (referred to as "CNDIFc" below). The inventive cyclic ligand comprises ferrocenyl group, two amide bonds or groups bonded with both ends of ferrocenyl group, naphthalene diimide moiety, and two connecting groups each connecting each amide bond or group and each N-terminal of naphthalene diimide moiety.

The DNA threading intercalating moiety may preferably comprise an aromatic group selected from a group consisting of 1, 4, 5, 8-tetrasubstituted naphthalene, 9, 10-disubstituted anthracene and 1, 5-disubstituted anthraquinone. The connecting manner (the positions of substitution) of the aromatic group plays decisive role as to whether the aromatic group works as the threading intercalating moiety (threading intercalator).

The cyclic ligand may further comprise two linker moieties each having two terminal amino groups. Each linker moiety is connected with the DNA threading intercalating moiety through one of its terminal amino groups and is connected with the ferrocenyl group through the other of its terminal amino groups.

The linker moiety may preferably be a residual group of an amine having two terminal amino groups. The amine may preferably comprise another amino group and two alkyl groups. Each alkyl group is bonded with each terminal amino group and another amino group. In this case, the another amino group may preferably be piperazinyl group, methylamino group, or amino group, and most preferably piperazinyl group. The alkyl group may preferably be C1–6 alkyl group and more preferably be ethyl or propyl group. The amine may most preferably be one of the followings.

1,4-bis(3-aminopropyl)piperazine, 1,1'-bis(3-aminopropyl)methylamine, 1,1'-bis(2-aminoethyl)amine, 1,1'-bis(3-aminopropyl)amine, spermine and spermidine.

The DNA threading intercalating moiety may further comprise, in addition to the aromatic group, carbonyl groups, iminomethylene groups (C=NR, R is hydrogen or an alkyl group), or thiocarbonyl groups (—C=S), through which the intercalating moiety may be bonded with the terminal amino groups. When the aromatic group is naphthalene, the terminal amino groups may be bonded through carbonyl groups, iminomethylene groups, or thiocarbonyl groups to 1, 4, 5, 8 positions of naphthalene, to form, for example, two imide groups or naphthalene-diimide moiety. When the aromatic group is anthracene, the terminal amino groups are bonded through carbonyl groups, iminomethylene groups, or thiocarbonyl groups to 9 and 10 positions of anthracene. When the aromatic group is anthraquinone, the terminal amino groups are bonded through carbonyl groups, iminomethylene groups, or thiocarbonyl groups to 1 and 5 positions of anthraquinone.

Ferrocenyl group and the other terminal amino group of each linker moiety may preferably be bonded through methylene group or carbonyl group.

In most preferred production process of the ligand, one mole of 1, 4, 5, 8-naphthalene tetracarboxylic acid, its monoanhydride or dianhydride is reacted with two moles of a connecting compound having two N-terminals (terminal amino groups) to produce one mole of a diamino body. This diamino body has naphthalene diimide moiety and two connecting groups, each having one N-end (terminal amino group). The diamino body is then reacted with ferrocene dicarboxylic acid or its active ester to provide a cyclic ligand.

Figure 1:
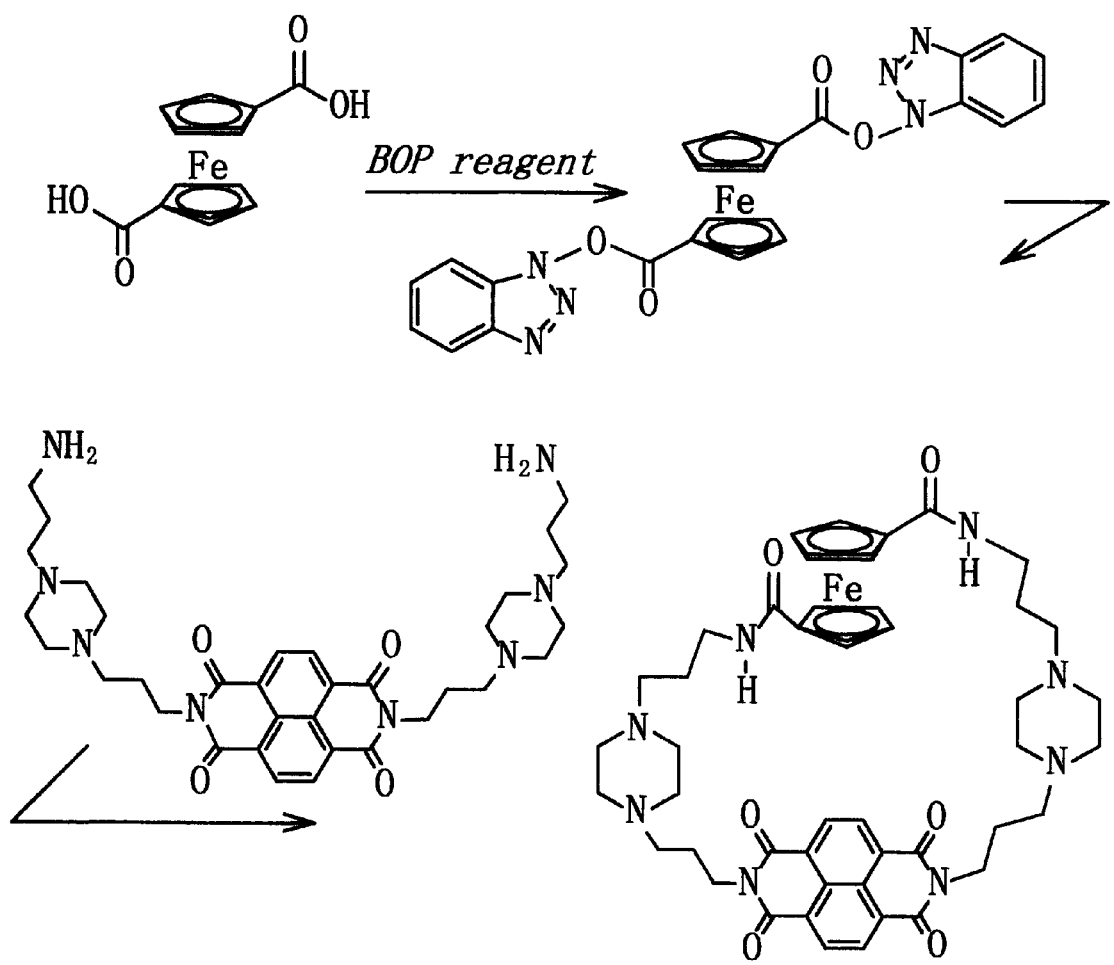
FIG. 1 is a synthesis scheme of a representative example (CNDIFc) of the inventive detection probe.

The invention will be described below in detail. The inventive detection device has a container holding solution containing the cyclic ligand, a working electrode modified with a gene, and a counter electrode to the working electrode, wherein the working electrode and counter electrode are dipped in the solution. The device may preferably be provided with a reference electrode.

The working, counter and reference electrodes may preferably made of, for example, gold, glassy carbon, or carbon. A gene to be detected may be immobilized onto the working electrode by means of a known method. For example, when the working electrode is made of gold, a thiol group may be introduced in a gene to bind it onto the working electrode by means of a gold-sulfur coordination bond. Such method for binding a gene with the working electrode of gold is described, for example, by B. A. Connolly, in a publication "Nucleic acids Res." 13, 4484, 1985. Moreover, a gene may be immobilized onto the working electrode made of glassy carbon by oxidizing the working electrode with potassium permanganate to introduce a carboxylic acid on the surface of the working electrode, and by binding the carboxylic acid with an amino acid constituting the nucleic acid of the gene. This method is described by Kelly M. Mollan and Susan R. Mikkelsen in a publication "Analytical Chemistry" 65, 2317–2323 (1993).

Preferably, a gene to be detected as such, or after replicating it by means of a polymerase chain reaction, is provided with a thiol group using mercaptoethanol and 1-ethyl-3-(3'-dimethylaminopropyl)-carbodiimide (WSCI), and then immobilized onto an electrode of gold by chemisorption. Alternatively, a gene to be detected as such, or after replicating it by means of a polymerase chain reaction using 5'-thiolated oligonucleotide as one of primers, is immobilized onto a gold electrode by chemisorption. This gold electrode functions as the working electrode. The inventive electrochemical determination is carried out in a cell containing the working, counter and reference electrodes in the presence of the cyclic ligand. Oxidation and reduction reactions of ferrocenyl group present in the inventive cyclic ligand induce current, whose amplitude may provide an indicator of whether a gene to be detected has a highly ordered structural site of single stranded nucleic acid or not and/or the content of the site. The amplitude of the induced current may be detected by a means or apparatus such as a cyclic voltamogram, a differential pulse voltamogram, or a potentiostat.

Phosphate buffered saline and the other salts may be added, in addition to the inventive cyclic ligand, to the solution. The solution may be adjusted as described below so that the inventive ligand specifically binds with the site and scarcely binds with a double stranded nucleic acid site. That is, the solution may preferably contain 1 to 50 $\mu$M (micromole) of the cyclic ligand, 10 to 100 mM of phosphate buffered saline, and 10 to 50 mM of a salt, the salt may preferably being a salt of an alkaline metal such as potassium or sodium.

EXAMPLES

The experimental results will be described below.

A cyclic ligand was synthesized according to the scheme of FIG. 1.

(synthesis of an amine body)

2 g of 1, 4, 5, 8-naphthalene tetracarboxylic acid dianhydride (7.45 mmol) and 40 ml of 1, 4-(3-aminopropyl) piperazine (190 mmol) are refluxed in tetrahydrofuran for 8 hours. After the mixture was cooled to room temperature, hexane was added to precipitate crystal, which was then collected by filtration. The thus obtained crystal was dissolved in a minimum volume of chloroform and recrystallized in ether. The resulting crystal was then removed, from which ether was vacuum-evaporated. The thus obtained crystal was dissolved again in chloroform and recrystallized in hexane. The resulting crystal was collected. The amount of the crystal was 330 mg and the yield was 52 percent. The crystal showed the following characteristics.

red-brown solid; melting point 300° C.; $^1$H-NMR chemical shifts (CDCl$_3$, ppm); 1.58, 1.95, 2.27–2.52, 2.71, 4.28, 8.75; IR C=O 1650 cm$^{-1}$;

(synthesis of an active ester of 1, 1'-ferrocene dicarbolylic acid)

0.14 g (0.5 mmol) of 1, 1'-ferrocene dicarboxylic acid was dissolved in 15 ml of DMF to obtain solution, to which 0.66 g (1.5 mmol) of POB reagent and 0.21 ml (1.5 mmol) of triethylamine dissolved in 5 ml of DMF were added dropwise. The resultant solution was stirred at room temperature for one and a half hour to obtain reagent solution containing an active ester of 1, 1'-ferrocene dicarboxylic acid. The reagent solution was used to a reaction with the above amine body.

(production of a cyclic ligand)

0.35 g (0.5 mmol) of the amine body was dissolved in 300 ml of chloroform. To the amine body solution, the reagent solution, containing an active ester of ferrocene dicarboxylic acid, was added dropwise while stirring the amine body solution. The resultant solution was then stirred at room temperature for 20 hours. The reaction solution was filtered to obtain filtrate, which was solidified at a reduced pressure and dissolved in methanol. The methanol solution was developed by silica gel column chromatography using methanol as its developing solvent to obtain a fraction seemingly containing a cyclic ligand. Methanol was removed at a reduced pressure from the fraction to provide precipitate, which was then dissolved in chloroform and washed with saturated sodium carbonate solution. Chloroform was removed from the solution to obtain crystal, which was dried at a reduced pressure and collected. 46 mg of crystal was obtained and its yield was 10 percent. The crystal showed the following characteristics.

yellow crystal; melting point 300° C.; $^1$H-NMR chemical shifts (CDCl$_3$, ppm); 1.56, 1.83, 1.99, 2.26, 2.45, 3.27, 4.28, 4.40, 4.43, 6.85, 8.77; IR C=0 1791, 1661 cm$^{-1}$;

| elemental analysis | H(%) | C(%) | N(%) |
|---|---|---|---|
| calculated: | 57.23 | 5.81 | 11.61 |
| measured: | 57.23 | 5.92 | 10.95 |

FAB mass spectrum: M+1 (871.5)

(Example of detection)

Figure 2:
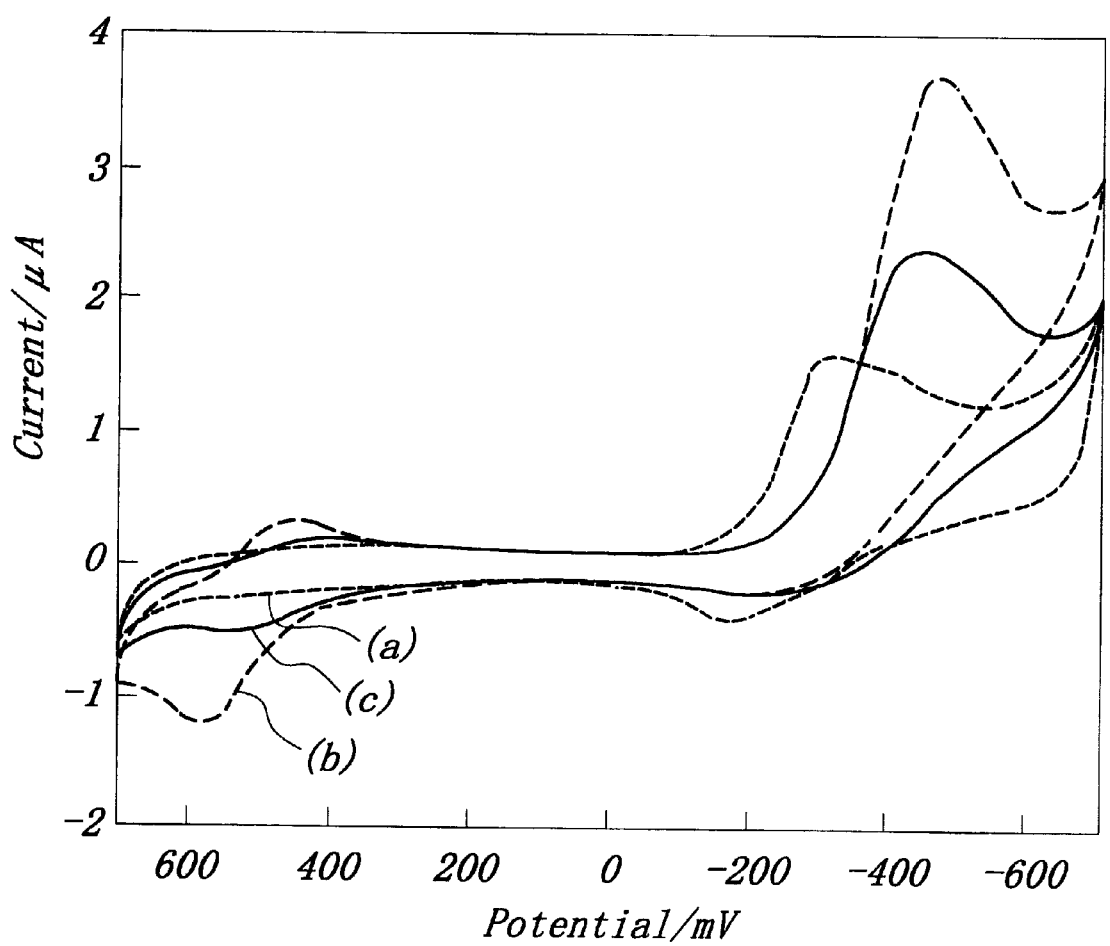
FIG. 2 is graphs showing examples of detecting a specific nucleic acid region, in which graph (a) is a cyclic voltamogram of CNDIFc using a working electrode made of gold modified with no gene, graph (b) is a cyclic voltamogram of CNDIFc using a working electrode made of gold modified with a hairpin structure DNA, and graph (c) is a cyclic voltamogram of CNDIFc after hybridizing the above hairpin structure with an oligonucleotide complementary with the hairpin structure DNA.

FIG. 2 shows detailed results of the detection of a hairpin structure composed of GCGAAAAACGC. A gold electrode modified with a hairpin type DNA (5'-HS-GCGAAAAACGC-3' was dipped in solution containing 10 mM of phosphate buffered saline (pH 7.0), 10 mM of KCl and 0.1 mM of CNDIFc. Ag/AgCl standard electrode (reference electrode) and a counter electrode of platinum were used to measure a cyclic voltamogram. The results were shown in graph (b) in FIG. 2. 1.2 μA of a response current was gained at 572 mV. That is, 20 pmol of hairpin structures provided a response current of 1.2 μA. Further, in this system, several femtomole of hairpin structure type DNA's were detectable. A response current at −457 mV was shown responding to the presence of naphthalene diimide.

Further, the above experiment was carried out using a gold electrode without any modification, providing results shown in graph (a). The above response current at 572 mV was not observed. The disappearance of the response current is reasonable, because ferrocenyl groups and naphthalene diimide moieties in CNDIFc's form charge transfer complexes in solution. Moreover, the response current corresponding to the presence of naphthalene diiuimide shifted to −312 mV and its amplitude was below ½ of that of the response current shown in the graph (b). Such results indicates that a charge transfer complex, with a charge transferred from ferrocene to naphthalene diimide, was formed in CNDIFc's in solution.

Contrary to this, in graph (b), current response at 572 mV was shown. This response may be explained as follows. Due to the interaction between CNDIFc and the structural site, bases constituting nucleic acids in the site are attached or sandwiched in CNDIFc's, inhibiting the above intermolecular charge transfer to induce measurable response current at 572 mV corresponding to ferrocene.

Further, in the above experiment, the hairpin structure DNA was hybridized with an oligonucleotide (5'-GCGTTTTTCGC-3') complementary to the hairpin DNA to cancel the hairpin structure site. The results were shown in graph (c), in which current response at 572 mV was disappeared. The results show that, even when a double stranded nucleic acid site coexists with a specific single stranded nucleic acid site the specific single stranded nucleic acid region may be detected. Further, the results definitely confirms that CNDIFc specifically binds to a highly ordered structural site of a single stranded nucleic acid and thereby provides current response on electrodes.

As described above, by contacting the inventive cyclic ligand containing naphthalene diimide moiety and ferrocenyl group with a working electrode modified with a gene and measuring its electro-chemical behavior or response currents by means of a cyclic voltamogram or differential pulse voltamogram, whether a highly ordered structural site of a single stranded nucleic acid is present in the gene (a DNA or RNA) or not, and/or the content of the site may be evaluated. Particularly, the inventive detection probe may show high sensitivity, because it provides an electrochemical response due to the inhibition of charge transfer between ferrocenyl group and naphthalene diimide moiety, only when the probe binds with the target site.

Although particular embodiments of the invention has been described above, it is understood that the embodiments may be modified without departing from the scope of the invention, which is limited only by the appended claims.

What is claimed is:

1. A probe for detecting a highly ordered structural site of a nucleic acid of a gene by specifically binding with the structural site to generate an electrochemical response, said probe comprising a cyclic ligand containing a ferrocenyl group bonded to a DNA threading intercalating moiety selected from the group consisting of 1,4,5,8-tetrasubstituted naphthalene and 1,5-disubstituted anthraquinone, wherein the cyclic ligand further comprises two linker moieties, wherein said linker moiety comprises an amine selected from the group consisting of 1,4-bis(3-aminopropyl) piperazine, 1,1'-bis(3-aminopropyl)methylamine, 1,1'-bis(2-aminoethyl)amine, 1,1'-bis(3-aminopropyl)amine, spermine and spermidine, each linker moiety, before it is incorporated into the cyclic ligand, has two terminal amino groups, each linker moiety is connected with the DNA threading intercalating moiety through one of said terminal amino groups, and each linker moiety is connected with the ferrocenyl group through the other said terminal amino group.

2. The probe of claim 1, wherein the DNA threading intercalating moiety comprises the aromatic group 1, 4, 5, 8-tetrasubstituted naphthalene.

3. The probe of claim 2, wherein the DNA threading intercalating moiety further comprises carbonyl groups, iminomethylene groups, or thiocarbonyl groups, through which the DNA threading intercalating moiety is bonded with the terminal amino groups.

4. The probe of claim 1, wherein the structural site of a nucleic acid is a high-order structure in a DNA or RNA.

5. The probe of claim 1, wherein the structural site of a nucleic acid is selected from a group consisting of a mismatch structure in an oncogenic DNA, a hairpin structure of a viral RNA and a bulge structure.

* * * * *